United States Patent [19]

Pantini et al.

[11] Patent Number: 4,959,171
[45] Date of Patent: Sep. 25, 1990

[54] SYNDET SOAP CAKES (SOAP BARS) HAVING IMPROVED PROPERTIES

[75] Inventors: Giovanni Pantini, Milan; Susanna Savonelli, Voghera, both of Italy

[73] Assignee: Ausimont S.r.l., Milan, Italy

[21] Appl. No.: 396,635

[22] Filed: Aug. 22, 1989

[30] Foreign Application Priority Data

Aug. 26, 1988 [IT] Italy ............... 21756 A/88

[51] Int. Cl.$^5$ ............... C11D 9/28; C11D 17/00; C08F 12/20; C08F 214/00
[52] U.S. Cl. ............... 252/174; 252/557; 252/554; 252/134; 252/132; 252/174.23; 252/89.1; 252/174.21; 252/DIG. 2; 252/DIG. 16; 526/247
[58] Field of Search ............... 526/247; 252/557, 554, 252/550, 174, 134, 132, 174.23, DIG. 16, DIG. 2, 89.1, 174.21

[56] References Cited

U.S. PATENT DOCUMENTS 3,665,041 5/1972 Sianesi et al. ............ 260/615 A
3,715,378 2/1973 Sianesi et al. ............ 260/463
4,066,746 1/1978 Callingham et al. ............ 424/62
4,518,520 5/1985 Foga ............ 252/174.23
4,587,316 5/1986 Nakagawa et al. ............ 526/247
4,638,041 1/1987 Ohmori et al. ............ 526/247

Primary Examiner—Dennis Albrecht
Assistant Examiner—James M. Silbermann
Attorney, Agent, or Firm—Stevens, Davis, Miller & Mosher

[57] ABSTRACT

Syndet soap cakes (soap bars) containing, besides the usual components, from 0.001 to 10% by weight of perfluoropolyethers having perfluoroalkyl end groups. Among the suitable perfluoropolyethers are those which contain one or more repeating perfluorooxyalkylene units selected from the group consisting of $(CF_2-CF_2O)$, $(CF_2O)$, $(C_3F_6O)$, $(CF_2O-CF_2-CF_2O)$, $(CF_2-CF_2CF_2O)$,

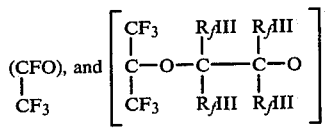

wherein the $R_fIII$ groups, which may be equal to, or different from, one another, are a fluorine atom or a perfluoroalkyl group.

5 Claims, 3 Drawing Sheets

SYNDET SOAP CAKES (SOAP BARS) HAVING IMPROVED PROPERTIES

DESCRIPTION OF THE INVENTION

The present invention relates to syndet soap cakes having improved properties.

Syndet soap cakes, also called "syndets" or "non-soap soaps," are, as is well known, soap cakes based on solid synthetic detergents.

As compared to the soap cakes manufactured from natural soap, they show several advantages. However, their use and manufacture suffer from drawbacks. The first drawback relates to the formation of clefts (cracks) in the soap cakes during use. Besides being unpleasant from an aesthetic viewpoint, this alteration may lead to the complete breaking down of the product.

On the other hand, the preparation of the syndet soap cakes, which is carried out on facilities designed for processing a more plastic product such as natural soap, presents difficulties owing to the higher stiffness of syndet soaps.

An object of the present invention is to provide syndet soaps wherein during use cleaving or cracking does not occur, or occurs only to a limited extent.

A further object of the invention is to make the preparation of the syndet soap cakes easier.

In accordance with this invention it has, surprisingly, been discovered that the addition to the syndet formulation of small amounts of perfluoropolyethers having perfluoroalkyl end groups eliminates or at least strongly reduces the phenomena of soap cake cleaving (cracking) and makes easier the preparation thereof, in that it provides a greater ease of homogenization of the compound in paste form, and makes it easier to be extruded and molded.

Therefore, the object of the present invention is syndet soap cakes containing, besides the usual components of such soap cakes, from 0.001 to 10% by weight of perfluoropolyethers having perfluoroalkyl end groups.

Figure 1A:
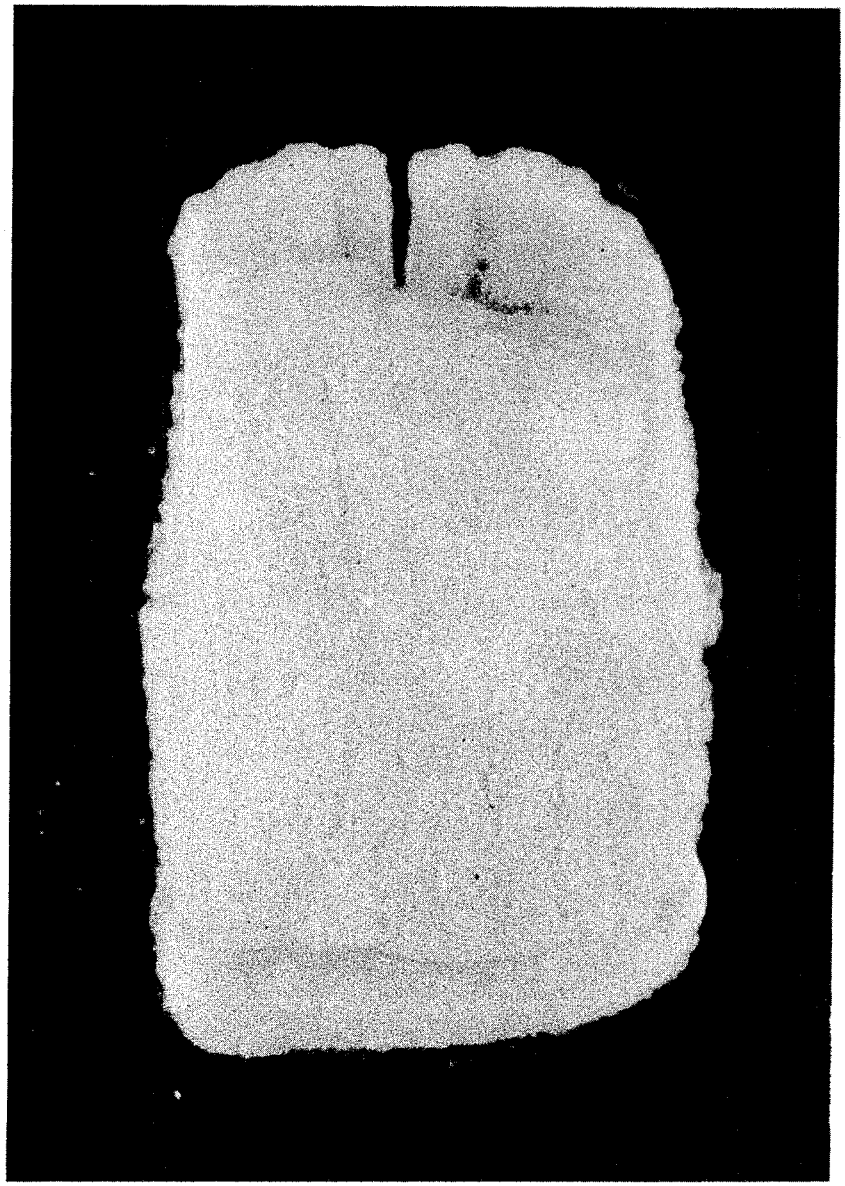
FIG. 1 shows two toilet bars the right hand bar contains the perfluoropolyether while the left bar is that of the prior art.

The perfluoropolyethers having perfluoroalkyl end groups, i.e., without functional groups, are per se well-known compounds which are disclosed, together with their method of preparation, in various documents among which may be mentioned U.K. Pat. No. 1,104,482; U.S. Pat. Nos. 3,242,218; 3,665,041; 3,715,378; and 4,532,039; European patent applications Nos. 148,482; 151,877; and 191,490, and international patent applications Nos. WO 87/00538 and WO 87/02992.

Among the suitable perfluoropolyethers are those which are characterized by the presence of one or more repeating perfluorooxyalkylene units selected from the group consisting of:

(a) $(CF_2-CF_2O)$;
(b) $(CF_2O)$;
(c) $(C_3F_6O)$, a simplified formula for indicating

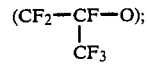

(d) $(CF_2O-CF_2-CF_2O)$;
(e) $(CF_2-CF_2-CF_2O)$;

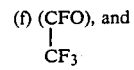

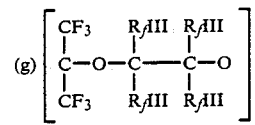

wherein the $R_fIII$ groups, which may be the same or different, are a fluorine atom or a perfluoroalkyl group.

The perfluoropolyethers suitable for the present invention contain preferably the following individual perfluorooxyalkylene units, or the following combinations of perfluorooxyalkylene units;

(I) $(CF_2-CF_2O)$ and $(CF_2O)$, with such units being randomly distributed along the perfluoropolyether chain; or (II)

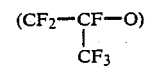

and (CFXO), wherein X is either F or $CF_3$, with such units being randomly distributed along the chain; or (III) $CF_2-CF_2O$,

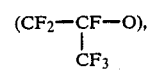

and (CFXO) wherein X is either F or $CF_3$, with such units being randomly distributed along the chain; or (IV)

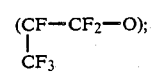

or (V) $(CF_2-CF_2-CF_2O)$; or
(VI) $(CF_2-CF_2O)$; or
(VII)

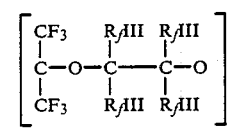

wherein the $R_fIII$ groups, which may be the same, or different, are a fluorine atom or a perfluoroalkyl group.

(VIII) $(CF_2O-CF_2-CF_2O)$.

Also the perfluoropolyethers which are suitable are those which contain perfluorooxetanic rings

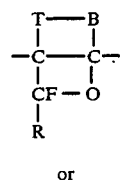

or

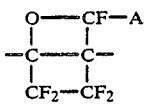

wherein,
T, B and R, which may be the same or different, are perfluorooxyalkyl, perfluoropolyoxyalkyl or perfluoroalkyl radicals, and A is a perfluoroxyalkyl, perfluoropolyoxyalkyl or perfluoroalkyl radical.

Examples of suitable perfluoropolyethers containing repeating perfluorooxyalkylene units are those belonging to the following classes.

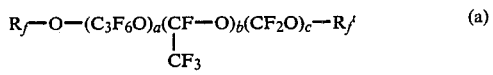  (a)

wherein:
$R_f$ and $R'_f$, which may be the same or different, are selected from the group consisting of $CF_3$, $C_2F_5$ and $C_3F_7$; the units consisting of $C_3F_6O$ (oxytrifluoromethyltrifluoroethylene),

and $CF_2-O$ being randomly distributed along the polymer chain;
a is an integer;
b and c are either integers or zero; with, when the total of (b+c) is different from zero, the ratio of a/(b+c) being from 5 to 40;

(b) $CF_3O-(C_2F_4O)_d(CF_2O)_e-CF_3$ wherein the $C_2F_4O$ and $CF_2O$ units are randomly distributed along the polymer chain; d and e are integers; and the radio of d/e is from 0.3 to 5;

(c) $CF_3O-(C_3F_6O)_f(C_2F_4O)_g(CFXO)_h-CF_3$ wherein
the $C_3F_6O$, $C_2F_4O$ and $CFXO$ units are randomly distributed along the polymer chain;
X is either F or $CF_3$;
f, g and h are integers; and
the ratio of f/(g+h) is from 1 to 50; and
the ratio of g/h is from 1 to 10;

(d) $R^3_fO-(CF_2CF_2CF_2O)_jR^4_f$ wherein $R^3_f$ and $R^4_f$, which may be the same or different from, each other, are either $-CF_3$ or $-C_2F_5$ and j is an integer.

The perfluoropolyethers suitable for use in the present invention have an average molecular weight which is commonly within the range of from 800 to 20,000, and is more commonly within the range of from 1,500 to 10,000.

The content of perfluoropolyether in the formulation is preferably within the range of from 0.1 to 2%.

The perfluoropolyether is usually added to the syndet formulation before this latter is homogenized.

Syndet soap cake pieces may be prepared as follows: As the starting formulation, a syndet base composition in powder form is used. Said base composition is mixed with water, perfluoropolyethers and other usual additives, and the whole product is homogenized; the product is extruded as rods, the rods are cut and the syndet soap cake pieces are molded on an automatic press.

The perfluoropolyethers employed according to the present invention show a perfect compatibility with the other components of soap cake, and do not modify to any meaningful extent the physical-chemical characteristics of the aqueous solutions of syndet soap cakes.

As the other components of the syndet soap cakes according to the present invention, all of the usual components of the above soap cakes may be used.

As the solid surfactants, the following are used, for exemplifying purposes:

(a') the isethionates, which are condensation products of a fatty acid of from 12 to 18 carbon atoms with sodium isethionate;

(b') the taurates, which are N-methyl-taurine amides of fatty acids of from 12-18 carbon atoms;

(c') the sulfates of fatty alcohols of from 12 to 18 carbon atoms;

(d') the sulfosuccinates of fatty alcohols of from 12 to 18 carbon atoms.

The organic acids used to adjust the pH of the aqueous solution of the soap cake at the desired value, are lactic acid and stearic acid.

All of the common plasticizers, such as e.g., the fatty acids, their esters and their alkanolamies, the fatty alcohols and the paraffins, may also be used. The customary fillers, such as polysaccharides and talc, may be used as well.

Also pigments, perfumes, and active principles may be used.

The addition of the perfluoropolyethers according to the present invention considerably improves the properties of the syndet soap cakes as said soap cakes do not show the phenomenon of cleaving during use, or, a least, show said phenomenon only to a very limited extent.

In the preparation of soap cakes, the paste-like compound is easier to be homogenized, and is easier to be extruded and molded.

The following examples are given for the purpose of merely illustrating the invention but without limiting it.

EXAMPLE 1

Several samples of syndet soap cakes were prepared containing a range of perfluoropolyethers according to the present invention (samples 2, 3, 5 and 6). For comparative purposes, syndet soap cakes were also prepared which did not contain any perfluoropolyethers (samples 1 and 4).

The following perfluoropolyethers manufactured by Montefluos were used:

(a) Fomblin HC/04, with an average molecular weight of 1,500 and a viscosity of 35 cSt at 20° C.;

(b) Fomblin HC/25, with an average molecular weight of 3,200 and a viscosity of 250 cSt at 20° C.;

(c) Fomblin HC/R, with an average molecular weight of 6,600 and a viscosity of 1,500 cSt at 20° C.;

All of them corresponded to the formula:

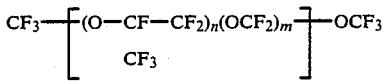

wherein the ratio m/m is from 20 to 40.

Two types of syndet bases were used:

(1) A preparation containing from 80 to 87% of sodium (coconut acid) isethionate;

(2) Zetesap 813A, by Zchimmer und Schwarz, which is a formulated base comprising

| | |
|---|---|
| a combination of sulfates and sulfosuccinates of fatty alcohols of from 12 to 18 carbon atoms; | 50% |
| a polysaccharide; | 23% |
| a plasticizer; | 23% |
| water and other ingredients | up to 100% |

Samples numbered from 1 to 6 as reported below were prepared; their composition is shown below in Table 1.

On an aqueous solution at 5% by weight of each one of these reported samples, the conductivity X, the pH value, and the surface tension, $T_{sup}$ were determined at a temperature of 25° C. The results are reported in Table 1.

A comparison between the samples containing various Fomblin HC grades, and the samples not containing them shows that the addition of the perfluoropolyether to the syndet soap cakes does not modify the above physical-chemical characteristics to any meaningful extent.

TABLE 1

| Sample No. | Composition | | X (Ms) | pH | δ (dyne$^{sup}$/cm) |
|---|---|---|---|---|---|
| 1 | Zetesap 813A | 100% | 3 3 | 7.10 | 30.3 |
| 2 | Zetesap 813A | 99.5% | 3.4 | 7.10 | 32.4 |
|   | Fomblin HC/25 | 0.5% | | | |
| 3 | Zetesap 813A | 98% | 2.9 | 6.55 | 31.0 |
|   | Fomblin HC/25 | 1% | | | |
|   | Perfume | 1% | | | |
| 4 | Sodium coconut acid Isethionate (80–87%) | 50% | 3.2 | 6.63 | 30.2 |
|   | Zetesap 813A | 50% | | | |
| 5 | Sodium coconut acid Isethionate (80–87%) | 50% | 3 | 6.51 | 30.3 |
|   | Zetesap 813A | 49% | | | |
|   | Fomblin HC/25 | 1% | | | |
| 6 | Sodium coconut acid Isethionate (80–87%) | 50% | 2.9 | 5.80 | 31.0 |
|   | Zetesap 813A | 49.4% | | | |
|   | Fomblin HC/25 | 0.4% | | | |
|   | Fomblin HC/R | 0.2 | | | |

EXAMPLE 2

This example reports the result obtained from a test of accelerated aging on use of a syndet soap cake containing Fomblin HC/25 (Sample 2 of Example 1), as compared to a similar syndet soap cakes not containing any perfluoropolyethers (Sample 1 of Example 1).

An accelerated aging of the soap cakes was simulated by dipping for 4 hours both of said soap cakes, having an approximate weight of 25 g, in running tap water at room temperature, then leaving them standing for 24 hours inside a ventilated oven at 30° C., with this treatment being repeated for 8 days.

After the above treatment, a meaningful difference was observed between the sample without Fomblin HC/25, and the sample which contained it; in fact, on the surface of the reference sample a larger number of more showy alterations were observed: bubbles, light or small-size but deep cleft or cracks; said reference soap cake was additionally affected by large crack at its edges. Furthermore, by measuring the weight loss, it was observed that a larger amount of the reference soap cake had been dissolved: in fact, 64% of the reference sample was dissolved, whilst 49% of the sample which contained Fomblin HC/25 was dissolved.

Figure 1B:
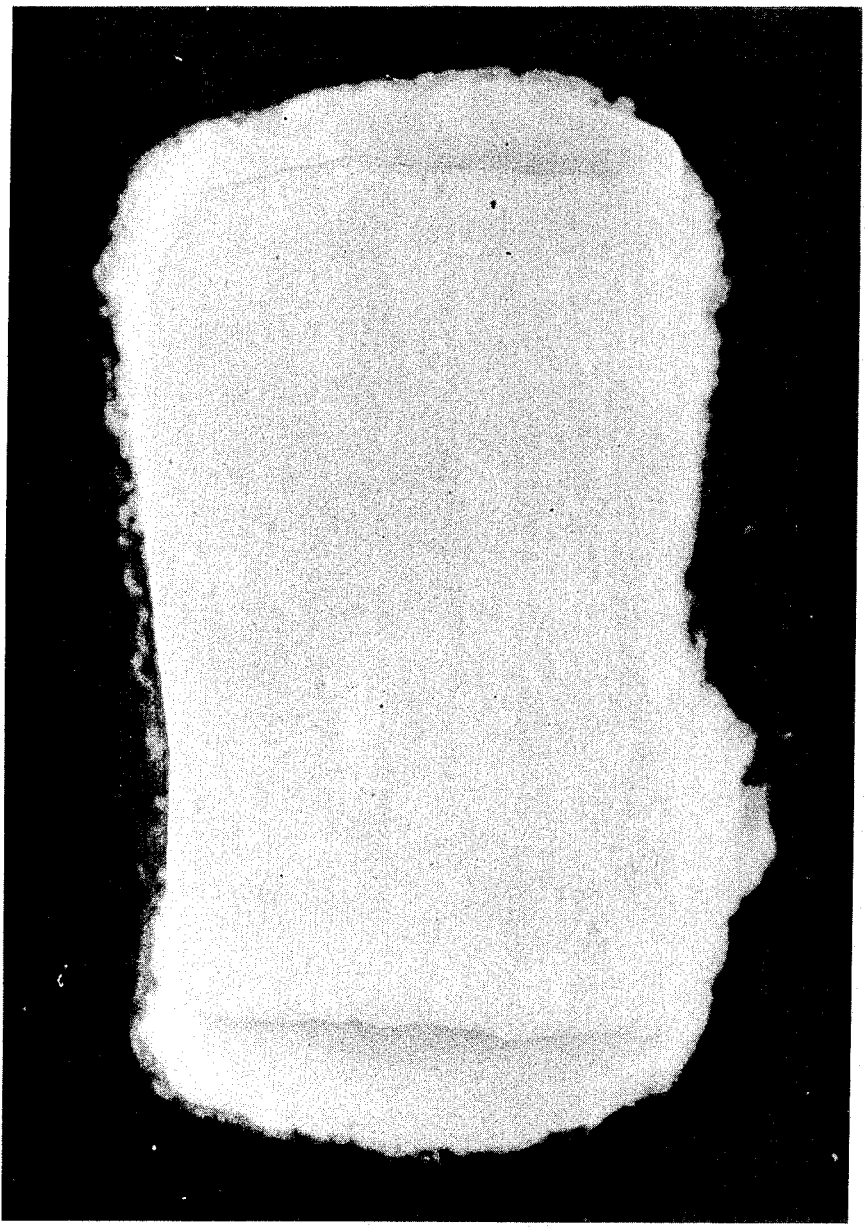

A photograph of the soap cakes, after the test, at a magnification of 2.5X, is shown in the accompanying FIGS. 1A and 1B. The right-hand side soap cake contained Fomblin HC/25; the left-hand soap cake is the reference sample which did not contain perfluoropolyether.

The above-mentioned alteration may be clearly seen in the reference sample.

EXAMPLE 3

This example reports the results obtained from an accelerated aging test on a syndet soap cake containing Fomblin HC/25 (Sample 7) in comparison with a similar syndet soap bar not containing any perfluoropolyether (Sample 8).

Sample 7 had the following composition:

| | |
|---|---|
| Sodium coconut acid isethionate (80–87%) | 17 parts |
| Fats, plasticizers and binding agents | 78 parts |
| Fomblin HC/25 | 0.5 part |
| Water | 5 parts |

Sample 8 had the following composition:

| | |
|---|---|
| Sodium coconut acid isethionate (80–87%) | 17 parts |
| Fats, plasticizers and binding agents (the same as in Sample 7) | 78 parts |
| Water | 5 parts |

An accelerated aging is simulated on the two bars having an approximate weight of 75 g by dipping them for 4 hours in running tap water at room temperature, then leaving them standing for 24 hours inside a ventilated oven at 30° C., with this treatment being repeated for 8 days.

Figure 2A:
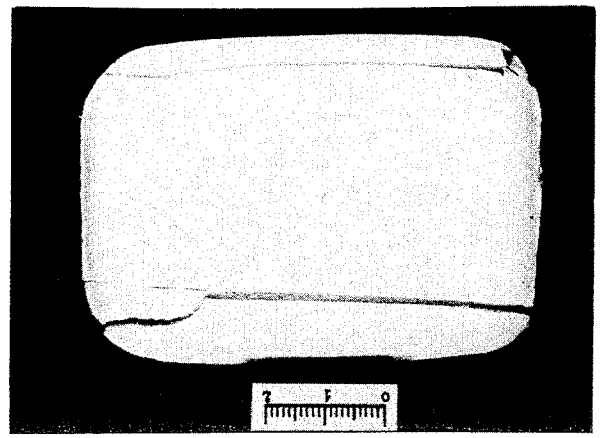
FIG. 2 shows two toilet bars the bar on the right side contains the perfluoropholyether while the left bar is that of the prior art. The figures show that the bars containing the perfluoropolyether have reduced cracking.
Figure 2B:
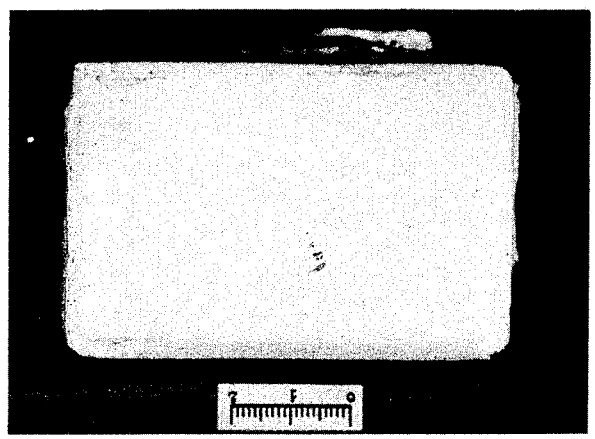

A photograph of the bars after the test is shown in FIGS. 2A and 2B. The bar on the right contained Fomblin HC/25, the bar on the left is the comparison sample not containing perfluoropolyether; large cracks are present in this sample 8.

What is claimed is:

1. Syndet bars containing besides the usual components of said cakes, from 0.001 to 10% by weight of perfluoropolyethers having end perfluoroalkyl groups to reduce cracking of said bars.

2. Syndet cakes according to claim 1, characterized in that the perfluoropolyethers contain one or more repeating perfluorooxyalkylene units selected from the group consisting of:
(a) $(CF_2—CF_2O)$;
(b) $(CF_2O)$;

(c) $(C_3F_6O)$,
(d) $(CF_2O-CF_2-CF_2O)$;
(e) $(CF_2-CF_2-CF_2O)$;

(f) $(CFO)$, and
   |
   $CF_3$ (g) 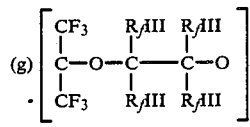

wherein the $R_fIII$ groups, which may be the same or different, are a fluorine atom or a perfluoroalkyl group.

3. Syndet cakes according to claim 1 or 2, characterized in that the perfluoropolyethers contain either individual repeating perfluorooxyalkylene units, or combinations of repeating perfluorooxyalkylene units selected from the group consisting of:

(I) $(CF_2-CF_2O)$ and $(CF_2O)$, with such units being randomly distributed along the perfluoropolyether chain; or (II)

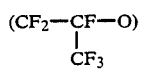

and $(CFXO)$, wherein X is either F or $CF_3$, with such units being randomly distributed along the chain; or (III) $(CF_2-CF_2O)$,

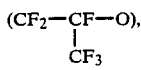

and $(CFXO)$ wherein X is either F or $CF_3$, with such units being randomly distributed along the chain; or (IV)

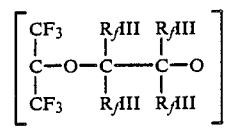

or (V) $(CF_2-CF_2-CF_2O)$; or
(VI) $(CF_2-CF_2O)$; or
(VII)

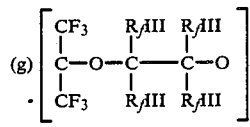

wherein the $R_fIII$ groups, which may be the same or different, are a fluorine atom or a perfluoroalkyl group, (VIII) $(CF_2O-CF_2-CF_2O)$.

4. Syndet cakes according to claim 1, characterized in that the perfluoropolyethers contain perfluorooxetanic rings of formula:

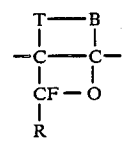

or

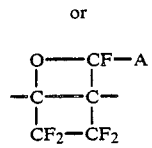

wherein,
T, B and R, which may be the same or different, are perfluorooxyalkyl, perfluoropolyoxyalkyl or perfluoroalkyl radicals, and
A is perfluorooxyalkyl, perfluoropolyoxyalkyl or perfluoroalkyl radical.

5. Syndet cakes according to claim 1 or 2 characterized in that the perfluoroalkylpolyethers have an average molecular weight within the range of from 800 to 20,000.

* * * * *